United States Patent [19]

Moore et al.

[11] Patent Number: 4,950,815

[45] Date of Patent: Aug. 21, 1990

[54] TETRAFLUOROETHANE ISOMERIZATION

[75] Inventors: Geoffrey J. Moore, Northwich; Helen M. Massey, Leigh, both of Great Britain

[73] Assignee: Imperial Chemical Industries PLC, London, United Kingdom

[21] Appl. No.: 424,108

[22] Filed: Oct. 20, 1989

[30] Foreign Application Priority Data

Oct. 20, 1988 [GB] United Kingdom ............... 8824571

[51] Int. Cl.$^5$ .................... C07C 17/10; C07C 17/24; C07C 19/02
[52] U.S. Cl. .................................. 570/151; 570/175; 570/176
[58] Field of Search ........................................ 570/151

[56] References Cited

U.S. PATENT DOCUMENTS 2,959,624  11/1960  Scherer et al. ...................... 570/151

FOREIGN PATENT DOCUMENTS 1039503  9/1958  Fed. Rep. of Germany ...... 570/151
121710  10/1978  Japan .................................. 570/151

OTHER PUBLICATIONS

Miller et al, "J. Am. Chem. Soc.", vol. 72 (1950), pp. 705–707.

Primary Examiner—J. E. Evans
Attorney, Agent, or Firm—Cushman, Darby & Cushman

[57] ABSTRACT

A method for the preparation of 1,1,1,2-tetrafluoroethane whereby 1,1,2,2-tetrafluoroethane is contacted with the fluorination catalyst at elevated temperature to effect isomerization.

7 Claims, No Drawings

TETRAFLUOROETHANE ISOMERIZATION

This invention relates to a chemical process and more particularly to a process for the manufacture of 1,1,1,2-tetrafluoroethane.

Several methods have been proposed for the manufacture of 1,1,1,2-tetrafluoroethane which is a useful refrigerant, aerosol propellant, blowing agent and solvent. Thus, our United Kingdom Pat. No. 1578933 describes a process for making tetrafluoroethanes by hydrogenating dichlorotetrafluoroethanes at elevated temperatures, for example temperatures in the range 200°–450° C. Also, our United Kingdom Pat. No. 2004539 describes the manufacture of 1,1,1,2-tetrafluoroethane by reacting trifluoroethylene in the vapour phase with hydrogen fluoride in the presence of chromium oxide, suitable reaction temperatures being in the range 200°–500° C. Both of these processes are expensive to operate.

It has now been found that 1,1,1,2-tetrafluoroethane can be prepared in high yield and high selectivity by the isomerisation of 1,1,2,2-tetrafluoroethane under the conditions hereinafter described.

Thus, according to the invention, there is provided a method for the preparation of 1,1,1,2-tetrafluoroethane which comprises contacting 1,1,2,2-tetrafluoroethane with a fluorination catalyst at an elevated temperature whereby to effect isomerisation.

Fluorination catalysts useful in the method of the invention have been fully described in the prior art and include aluminium fluoride, sodium fluoride, gammaalumina and, especially, chromia. Unmodified chromia may be used but it is advantageous to use a pre-fluorinated chromia that has been used in other fluorination reactions. After use, the catalyst may be regenerated by treatment with air at an elevated temperature, for example 400°–420° C.

The isomerisation temperature should be sufficiently high to effect conversion of the 1,1,2,2,-tetrafluoroethane but not so high that excessive amounts of by-products, such as pentafluoroethane, are obtained. In general, suitable temperatures are found in the range from about 300° to about 900° C. Lower temperatures can generally be employed when using chromia as the fluorination catalyst, for example temperatures from about 300° to about 550° C., more especially from 350° to 500° C. and preferably from 400° to 450° C. At these temperatures, the 1,1,2,2-tetrafluoroethane, optionally in conjunction with an inert diluent such as nitrogen, is suitably contacted with the catalyst for times of between about 1 and about 50 seconds.

The 1,1,2,2-tetrafluoroethane use as starting material in the method of the invention may be obtained by known methods, for example by the method described in United Kingdom Pat. No. 1578933 or by the hydrogenation of tetrafluoroethylene. The latter reaction may be conveniently effected at normal or elevated temperatures, for example up to 250° C., in the presence of a hydrogenation catalyst, for example palladium on alumina.

The invention is illustrated but not limited by the following Example.

EXAMPLE

Hydrogenation of Tetrafluoroethylene

Hydrogen at 1000 ml/min and tetrafluoroethylene at 100 ml/min were passed over 120 g 5% palladium-/alumina at ambient temperature in a glass reactor, the off gases being collected in two traps cooled in trichloroethylene and Drikold. There was an immediate exotherm and the temperature rose to 250° C. After 210 min, the hydrogen and tetrafluoroethylene flows were turned off and the reactor and lines purged with nitrogen. The material condensed in the traps was weighed and analysed. The product was 84.4 g (94% yield) of 1,1,2,2-tetrafluoroethane (purity 98.5%).

Isomerisation of 1,1,2,2,-Tetrafluoroethane 1,1,2,2-Tetrafluoroethane and diluent nitrogen were passed through a Hastelloy reactor tube packed with 80 ml chromia, the reactor being heated in a furnace. After the reactor, the gases were passed through an empty tube to effect cooling and then through a scrubber containing 25% potassium hydroxide solution to remove hydrogen fluoride. The products were finally condensed in a trap cooled in trichloroethylene and Drikold. Gas samples were taken after the scrubber for analysis by gas chromatography.

Details of a number of runs using pre-fluorinated chromia, which had been dried at 400° C. for 4 hours and then "activated" by passage of air at 200–300 ml/min at 400° C. overnight, are given below in Table 1. In the Table:

A134 = 1,1,2,2-tetrafluoroethane
A134a = 1,1,1,2-tetrafluoroethane
3FE = trifluoroethylene
A125 = pentafluoroethane A flow rate of 50 ml/min A134 and 100 ml/min nitrogen corresponds to a catalyst contact time of approximately 12 sec.

Table 2 gives details of runs using the same catalyst after regeneration with 400 ml/min air at 400° C. for 16 hours.

TABLE 1

| Catalyst Volume ml | Temperature °C. | A134 Flowrate ml/min | Nitrogen Flowrate ml/min | Concentration in Off Gas mole % | | | |
|---|---|---|---|---|---|---|---|
| | | | | A134 | A134a | 3FE | A125 |
| 80 | 288 | 50 | 100 | 93.5 | 1.0 | 0.1 | 0.2 |
| 80 | 325 | 50 | 100 | 91.4 | 3.0 | 0.1 | 0.4 |
| 80 | 420 | 50 | 100 | 69.9 | 21.5 | 0.2 | 0.7 |
| 80 | 460 | 50 | 100 | 59.4 | 34.1 | 0.3 | 1.8 |
| 80 | 497 | 50 | 100 | 52.6 | 34.6 | 0.2 | 8.5 |
| 80 | 550 | 50 | 100 | 48.1 | 28.1 | 0.3 | 27.9 |
| 80 | 510 | 50 | 100 | 56.0 | 26.0 | 0.6 | 12.7 |
| 80 | 465 | 50 | 100 | 73.4 | 21.0 | 1.0 | 2.7 |
| 80 | 410 | 50 | 100 | 88.5 | 9.1 | 0.6 | 0.4 |
| 80 | 470 | 50 | 100 | 74.9 | 19.4 | 0.2 | 3.8 |

TABLE 2

| 80 | 420 | 50 | 100 | 29.1 | 4.2 | — | 60.2 |
|---|---|---|---|---|---|---|---|
| 80 | 343 | 50 | 100 | 66.9 | 25.7 | 0.4 | 3.7 |
| 80 | 328 | 50 | 100 | 75.5 | 21.1 | — | 1.1 |
| 80 | 375 | 50 | 100 | 43.6 | 48.8 | 0.1 | 5.4 |
| 80 | 388 | 50 | 200 | 52.3 | 43.0 | 0.2 | 2.8 |
| 80 | 400 | 50 | 300 | 46.3 | 48.1 | 0.1 | 3.9 |
| 80 | 412 | 50 | 400 | 49.8 | 44.3 | 0.1 | 4.4 |
| 80 | 410 | 50 | 200 | 40.3 | 50.2 | 0.9 | 7.1 |
| 80 | 430 | 50 | 300 | 47.1 | 43.6 | 1.6 | 6.2 |
| 80 | 440 | 50 | 400 | 53.1 | 36.8 | 2.2 | 6.5 |
| 80 | 445 | 50 | 100 | 28.4 | 52.9 | 0.5 | 16.6 |
| 80 | 450 | 50 | 150 | 41.4 | 45.1 | 0.7 | 11.1 |
| 80 | 455 | 50 | 100 | 40.6 | 42.5 | 0.6 | 14.7 |
| 80 | 455 | 50 | 100 | 47.9 | 42.2 | 0.8 | 7.9 |

I claim:

1. A method for the preparation of 1,1,1,2-tetrafluoroethane which comprises contacting 1,1,2,2-tetrafluoroethane with a fluorination catalyst at an elevated temperature whereby to effect isomerisation.

2. A method according to claim 1 wherein the catalyst comprises chromia.

3. A method according to claim 2 wherein the catalyst comprises pre-fluorinated chromia.

4. A method according to any preceding claim wherein the temperature is in the range from about 300° to about 900° C.

5. A method according to claim 4 wherein the temperature is in the range from about 300° to about 550° C.

6. A method according to claim 5 wherein the temperature is in the range from 350° to 500° C.

7. A method according to claim 6 wherein the temperature is in the range from 400° to 450° C.

* * * * *